US007381197B2

United States Patent
Kelly et al.

(10) Patent No.: US 7,381,197 B2
(45) Date of Patent: Jun. 3, 2008

(54) ELECTRIC BREAST PUMP

(76) Inventors: Patricia A. Kelly, 2545 Keystone St., Burbank, CA (US) 91504; Joan P. Ortiz, 1930 N. Valley St., Burbank, CA (US) 91504; David R. McCusker, 4401 Palm La., Shingle Springs, CA (US) 95682

( * ) Notice: Subject to any disclaimer, the term of this patent is extended or adjusted under 35 U.S.C. 154(b) by 517 days.

(21) Appl. No.: 10/644,199

(22) Filed: Aug. 20, 2003

(65) Prior Publication Data
US 2005/0043677 A1  Feb. 24, 2005

(51) Int. Cl.
*A61M 1/06* (2006.01)
(52) U.S. Cl. ...................................... 604/74
(58) Field of Classification Search ............ 604/74–76, 604/35, 36, 118; 119/14.47, 14.49
See application file for complete search history.

(56) References Cited

U.S. PATENT DOCUMENTS

| 4,799,922 | A * | 1/1989 | Beer et al. ............... 604/74 |
| 5,885,246 | A * | 3/1999 | Ford ......................... 604/74 |
| 6,045,529 | A | 4/2000 | Nuesch |
| 6,383,163 | B1 | 5/2002 | Kelly et al. |
| 6,579,258 | B1* | 6/2003 | Atkin et al. .............. 604/74 |
| 6,663,587 | B2* | 12/2003 | Silver et al. .............. 604/74 |
| 2002/0193731 | A1* | 12/2002 | Myers et al. ............. 604/74 |

OTHER PUBLICATIONS

Vincent, Monty E., et al., "Evaluation of Vacuumi Suction Safety Devices in Preventing Transmission of Human Virus Pathogens", American Clinic Laboratory, Jan. 1989.
Blenkharn, J. Ian, "Infection Risks From Electrically Operated Breast Pumps", Journal of Hospital Infection, 1989, 13, 27-31.
Donowitz, Frederic J., "Contaminated Breast Milk: A Source of Klebsiella Bacteremia in a Newborn Intensive Care Unit", The University fo Chicago, Review of Infectious Diseases, vol. 3, No. 4, Jul.-Aug. 1981.
Fewtrell, M.D., Mary S., "Randomized Trial Comparing the Efficacy of a Novel Manual Breast Pump with a Standard Electric Breast Pump in Mothers Who Delivered Preterm Infants", Pediatrics, vol. 107, No. 6, Jun. 2001.

* cited by examiner

*Primary Examiner*—Matthew F Desanto
(74) *Attorney, Agent, or Firm*—Kenneth L. Green; Edgar W. Averill, Jr.

(57) ABSTRACT

A vacuum control system controls the amount of time that pressure is applied to a breast and the amount of time no pressure is applied to the breast, independent of the vacuum level. The amount of time that pressure is applied to a breast and the amount of vacuum applied to the breast cups can be varied by the user. A disposable biological filter isolates the pump from the breast cups. The biological filter is packaged in a housing that has an O-ring push-in connector to connect the collection system to the pump. The vacuum applied to the breast cups is monitored. The control system maintains the vacuum at a level set by the user. A second higher level is used as a safety threshold. The control system shuts down the pump when this higher level is sensed. The breast cup is constructed to provide a controlled collapse when vacuum is applied to mimic the suckling of an infant.

21 Claims, 8 Drawing Sheets

ELECTRIC BREAST PUMP

BACKGROUND OF THE INVENTION

1. Field of the Invention

The present invention relates generally to improvements in breast pumps and, more particularly, pertains to a new and improved method and apparatus for extracting milk from the breast.

2. Description of Related Art

Most prior art breast pumps designed for extracting milk are concerned only with controlling the rate at which a negative pressure is applied to the breast and, in some cases, the amount of negative pressure. An example of an electric breast pump which does more than this is illustrated in the U.S. Pat. No. 6,383,163 granted May 7, 2002 to two of the three named joint inventors of the present invention. The disclosure of U.S. Pat. No. 6,383,163 is expressly incorporated herein by reference.

Although the prior art breast pumps and, specifically, the prior art breast pump described and claimed in U.S. Pat. No. 6,383,163 are very effective, these prior art pumps do not contemplate controlling the refractory time of the suction cycle. The result is that the pump is not as efficient as it could be in removing the breast milk. As a result of this decreased efficiency, a longer overall pumping period is required. The longer period increases the physical demands on the user. Moreover, most prior art breast pumps only apply a suction face to the breast for expressing the mother's milk.

The present invention, on the other hand, is much more efficient than the prior art devices. The present invention allows the user to control the amount of time within a suction cycle that pressure is applied to the breast and the amount of time that no pressure is applied to the breast, independently of the frequency of the suction cycle. Control of the refractory time results in a substantial increase in the amount of milk collected over a given time period. The use of a breast cup that collapses in a progressive manner mimicking a suckling infant facilitates an efficient or comfortable expression of the mother's milk.

SUMMARY OF THE INVENTION

A vacuum control circuit controls the amount of time pressure is applied to the breast and the amount of time no pressure is applied to the breast within each suction cycle. The cycle rate of the pump is selected by the user and is independent of the user's selected pressure and refractory time. Both the pressure and refractory time are independent of one another. A disposable biological filter isolates the breast cup from the pump. The biological filter connects the milk collection system to the pump by an easily engageable push-on connector mechanism. The vacuum level applied to the breast cup is electronically monitored. The vacuum control circuit controls a valve in the vacuum line to keep the vacuum at a level set by the user. A second predetermined higher vacuum level set into the control circuit is used as a safety threshold. The vacuum pump is shut down by the control circuit when this higher level is sensed. The breast cup is designed to collapse in a progressively controlled way so that the areola area of the breast is squeezed first and then the teat.

BRIEF DESCRIPTION OF THE DRAWINGS

The exact nature of this invention, as well as the objects and advantages thereof, will become readily apparent from consideration of the following specification in conjunction with the accompanying drawings in which like reference numerals designate like parts throughout the figures thereof and wherein.

DETAILED DESCRIPTION OF THE PREFERRED EMBODIMENTS

Reference will now be made to the preferred embodiments of the invention, examples of which are illustrated in the accompanying drawings. While the invention will be described in conjunction with the preferred embodiments, it will be understood that these embodiments are not intended to limit the invention. On the contrary, the intention is intended to cover alternatives, modifications and equivalents, which may be included within the spirit and scope of the invention as defined by the appended claims. In the following detailed description, numerous specific details are set forth in order to provide a thorough understanding of the present invention. However, it will be understood by one of ordinary skill in the art that the present invention may be practiced without these specific details. In other instances, well known methods, procedures, components, and circuits have not been described in detail so as not to unnecessarily obscure the important aspects of the present invention.

Figure 1:
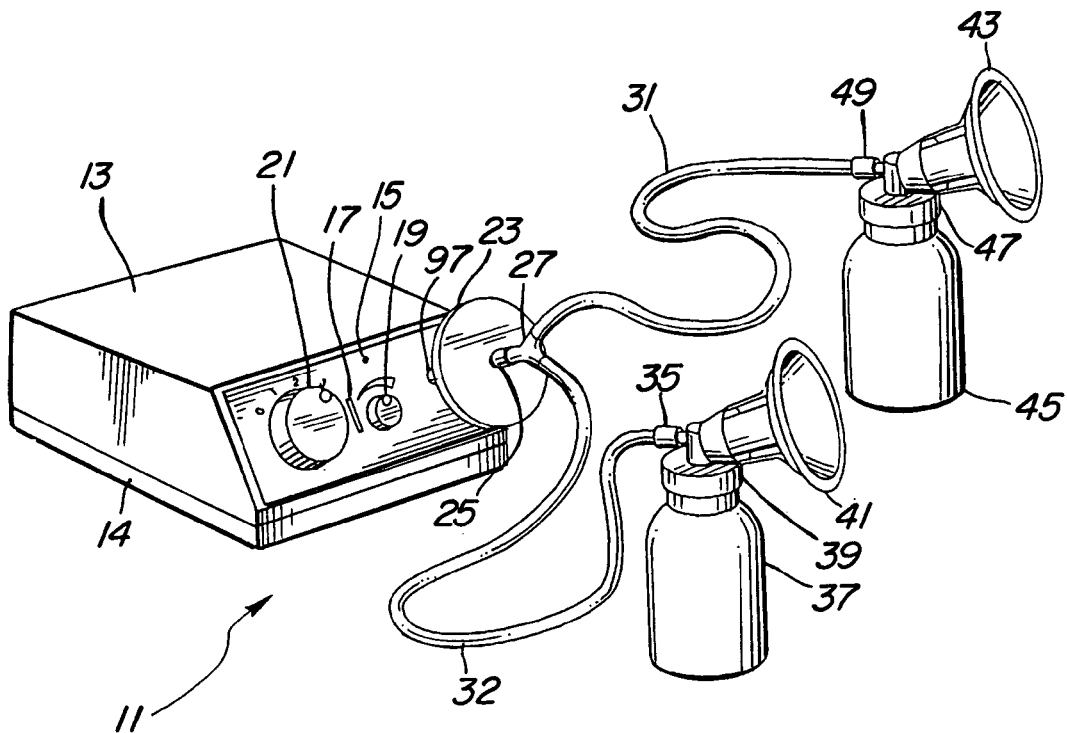
FIG. 1 is a perspective illustration of the basic elements of a preferred embodiment of the present invention.

Referring now to FIG. 1, the breast pump 11 of the present invention is illustrated as contained within a housing having a top 13 and a base 14, preferably made of a light-weight plastic. The housing contains a pump control circuit and sensing elements which will be hereinafter described. The housing top 13 has manually operable controls for the user such as an on-off switch and cycle control knob 21, and vacuum control knob 19. A timer indicating light 17 and on-off fault indicator LED 15 tells the user about the function of the pump 11. The time indicating light 17 tells the user how much time is left in a session.

A disposable isolation filter 23 is shown attached to the pump connector 97 through the front panel of the housing top 13. Exactly how the filter 23 is connected will be described hereinafter. A short length of tubing 25 attaches to the inlet side of filter 23. Because the illustration is for a two breast cup system, a Y-connector 27 connects tube line 25 to a pair of vacuum lines 31, 32 which lead to respective collection bottles and breast cups. Vacuum line 31 is connected to a breast cup 43 by way of a tube connector 49. Vacuum tube or line 32 is connected to breast cup 41 by way of a tube connector 35. Each breast cup 43 and 41 is symmetrical and made of a soft flexible material, such as silicone rubber constructed to provide a controlled collapse in operation. Each breast cup is shaped to comfortably fit over the human teat and a portion of the breast. Each breast cup is associated with its respective collection bottle. Breast cup 41, besides being connected to vacuum line 32, connects to the interior of collection bottle 37 by a removable cap 39. Likewise, breast cup 43 is connected to connection bottle 45 by a removable cap 47.

Figure 2:
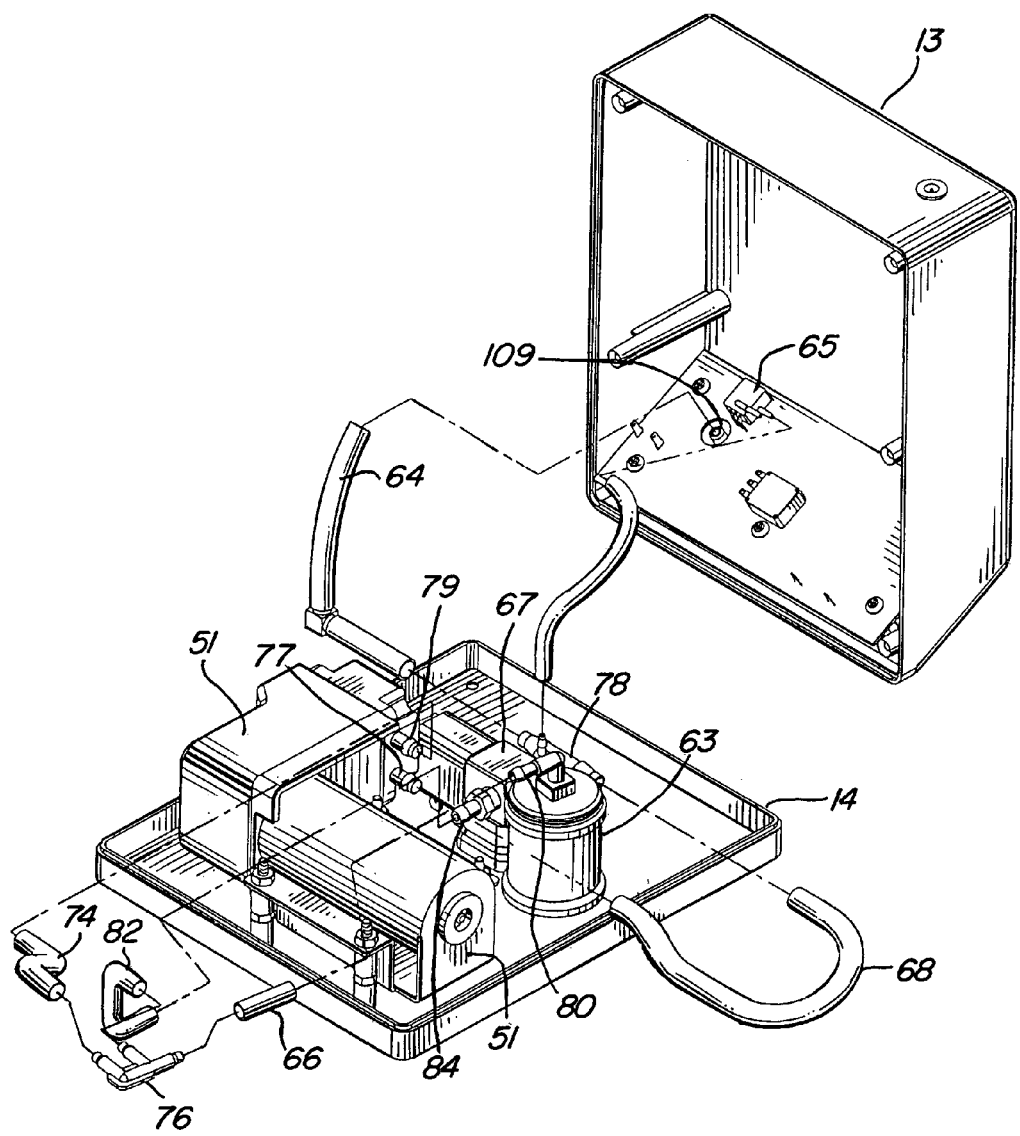
FIG. 2 is a perspective exploded illustration of a preferred embodiment of the pumping and control elements of the present invention.

Referring now to FIG. 2, an exploded perspective of the inside of the housing with the top 13 separated from the bottom 14, is illustrated.

A motor-driven piston vacuum pump 51 is mounted to the bottom 14 of the housing. The inlet side 77 of pump 51 is connected by way of vacuum line 68, four-way connector 74 and vacuum line 64 to the back side connection 109 of isolation filter connector 97. Besides connecting vacuum lines 68 and 64 together, four-way connector 78 connects to the input side (not shown) of line valve 67. The output side 84 of line valve 67 is connected by way of line 82, T-connector 76 and line 66 to the input 80 of the exhaust filter 63. The output side 84 of the line valve 67 is also connected by way of line 82, T-connector 76 and line 74 to the output end 79 of the pump 15. A vacuum sensor 65 mounted to the top 13 of the housing, senses the vacuum level in the system by being connected to four-way connector 78 over line 68.

Figure 3:
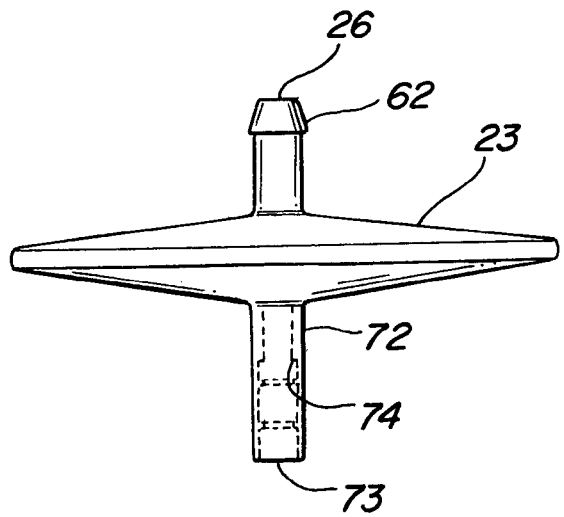
FIG. 3 is a front plan view of a preferred embodiment of an input isolation filter used in the present invention.

FIG. 3 illustrates in greater detail the biological isolation filter 23 shown and referred to in FIG. 1. Biological filter 23 is contained within a polypropylene housing which is preferably rated at 15 psi or better. The filter is unidirectional in that air flows only from the inlet side 26 to the outlet side 73. The inlet side preferably contains a quarter-inch single hose barb connector 62. The outlet side 73 is a cylindrical extension 72 with a step-down interior diameter creating a ledge 74 on the inside. The filter media utilized for biological filter 23 is preferably a 1.0 micron PTFE at 60 mm.

Figure 4:
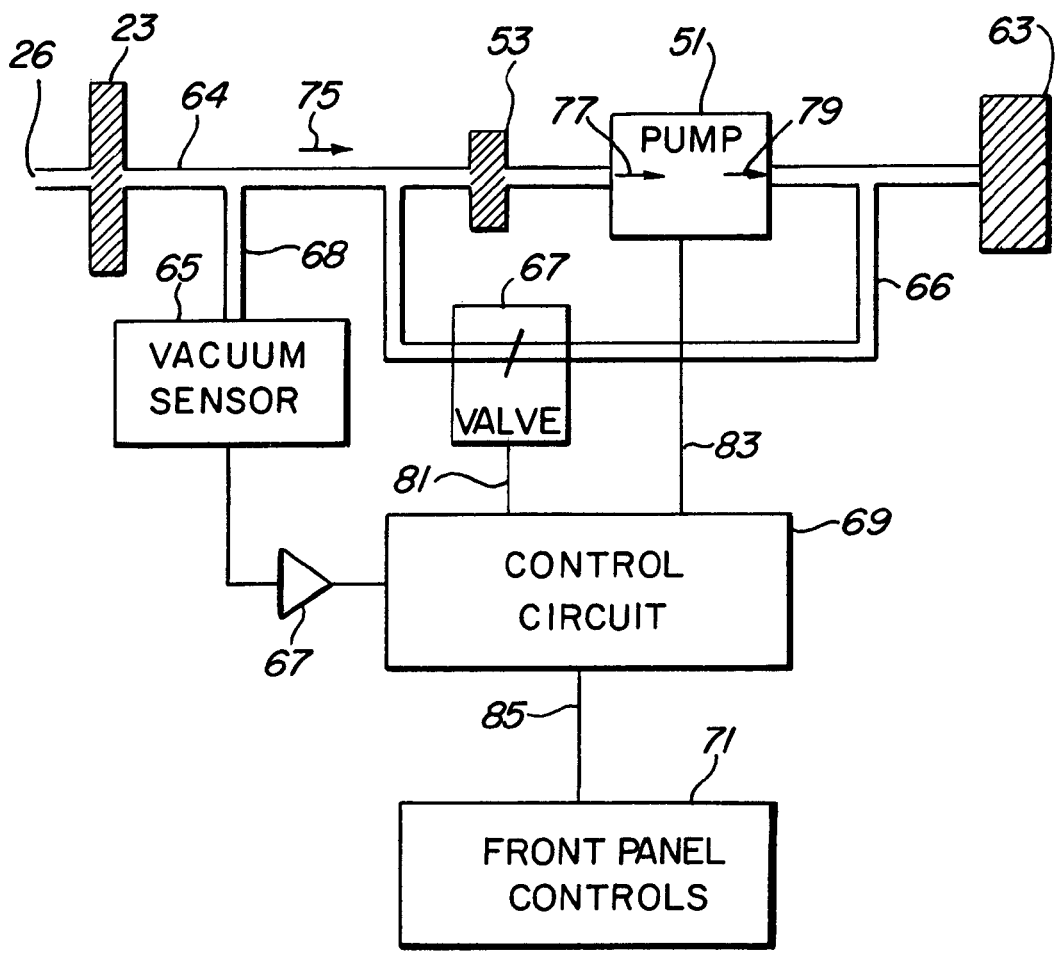
FIG. 4 is a block diagram schematic showing all the preferred operative elements of the present invention.
Figure 5:
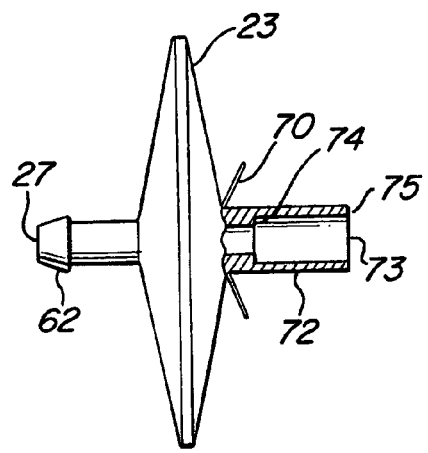
FIG. 5 is a plan view, partially broken away of the input isolation filter.

Referring now to FIG. 4, the functional elements of the breast pump system contained within the housing is illustrated. The pump 51 is shown connected into the vacuum line 64 at its input side 77. Biological isolation filter 23 also connects to vacuum line 64. The input 26 of biological filter 23 is connected to breast cups 43 and 41 (FIG. 1) by way of their respective vacuum lines 31 and 32.

A second biological filter 53 may be located at the physical input 77 of pump 51 between the pump input 77 and the line valve 67. A third exhaust filter 63 is located at the physical output 79 of pump 51 after the output line 66 of the line valve 67. The vacuum line 66 connects or shunts around pump 51 from the input side of biological filter 53 to the output side of pump 71, at the input side of the third biological exhaust filter 63.

An electrically operated solenoid valve 67 which is controlled over line 81 by a control circuit 69 is connected into the shunt vacuum line 66. A vacuum sensor 65 which constantly monitors the level of vacuum in the system is connected to vacuum line 64 by vacuum line 68. Vacuum line 64 is connected through biological filter 23 to the breast cups (FIG. 1).

The signal from the vacuum sensor 65 is amplified by a sensor amplifier 67 before being provided to the control circuit 69. The control circuit 69 responds to the signal from the vacuum sensor to control both the pump 51 and the valve 67 in a manner which will be described hereinafter. The control circuit 69 also responds to front panel controls 71 which are illustrated in FIG. 1 as including the on-off/vacuum cycle knob 21, and the vacuum control knob 19.

Referring now to FIGS. 5, 6, 7 and 8, the easy insertion and removable feature associated with the biological filter 23, is illustrated. The unidirectional flow filter 23 connects to the pump 51 by way of a quick connect and release mechanism that is vacuum tight. The output end 73 of filter 23 has a cylindrical extension 72 broken away at line 70, to show the two distinct internal diameters creating a ledge 74 at the interface between the larger diameter 75 at the output end 73 and the smaller diameter at the filter end 23.

Figure 6:
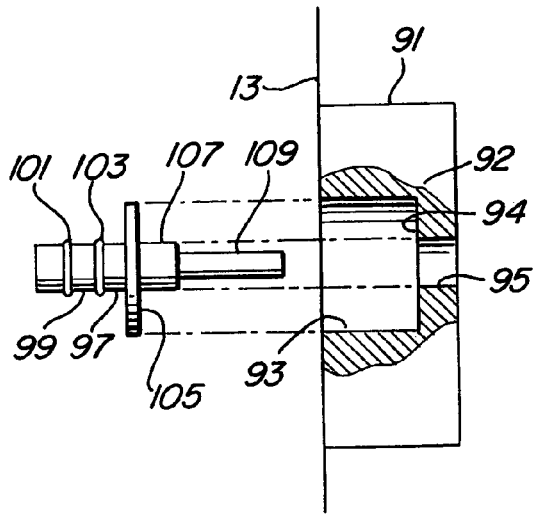
FIG. 6 is an exploded view, partially broken away, of the input isolation filter connector mounted in the pump housing.
Figure 7:
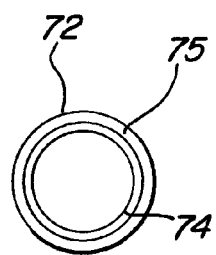
FIG. 7 is an end view of the filter of FIG. 5.
Figure 8:
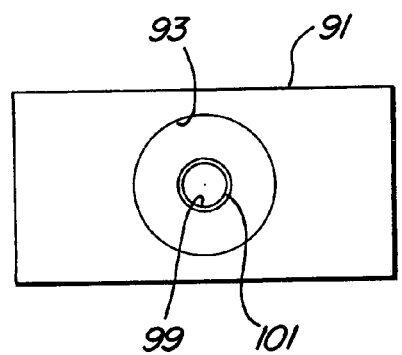
FIG. 8 is a front plan view of the filter connector of FIG. 6.

A connector block 91 is mounted to the underside of the face plate on the top 13 of the housing. The connector block 91 of FIG. 6 is broken away at 92 to show the two diameter pass-through apertures in the block 91. The larger diameter cylindrical aperture 93 defines the size of the aperture in the face plate of the housing. The smaller diameter cylindrical aperture 95 extends from the larger diameter aperture to the other side of the connector block 91. The difference in diameter between the two, creates a mounting ledge 94 in the larger aperture 93 of the connector block 91.

A male connector 97 is mounted inside the cylindrical aperture 93 of the connector block 91 against the mounting ledge 94. FIG. 6 shows the male connector 97 outside of the connector block for clarity of illustration. In assembled form, the shaft 99 of connector 97 is located within cylindrical aperture 93 with the mounting ring 105 of the male connector 97 fastened against ledge 94 in any convenient manner. The backside 107 of shaft 99 on the other side of mounting ring 105 extends through cylindrical aperture 95 to the other end of the connector block 91. The backside 107 of the connector 97 is stepped down to a smaller diameter cylinder 109 for connection to the vacuum lines 64 inside the housing.

The first isolation filter 23 attaches to the connector 97 inside the connector block 91 by fitting the cylindrical extension 72 of the filter 23 over the shaft 99 of the male connector 97. To insure a vacuum-tight fit between the filter 23 and the male connector 97, a pair of O-rings of appropriate size are displaced along the length of the shaft 99. In addition, the shaft extension is preferably tapered at about six degrees (6°) from its base at the mounting ring 105 to the tip. Furthermore, the inside O-ring may be slightly larger in diameter than the outside O-ring 101.

The result of this structure is a quick-connect/disconnect connection that gets tighter as the vacuum level increases. As the vacuum goes up, cylindrical extension 72 of the filter 23 is pulled further along the shaft 97 of the connector 97 to the mounting, creating a tighter fit.

When a user desires to make a connection between the collection system and the vacuum pump inside the housing, cylindrical extension 72 is simply inserted over shaft 99 of male connector 97 which is mounted inside of the connector block 91 on the panel of the housing. The two O-rings 101 and 103, along with the tapered shaft extension, insure that the connection is vacuum tight even though the filter may be easily inserted and removed. This structure also enables easy replacement of the filter.

The function of the breast pump in the housing is to provide a vacuum at male connector 97 to which the biological isolation filter 23 is removably connected. The vacuum lines connected to the biological isolation filter 23 carry the vacuum to the breast cup.

At startup, valve 67 in the vacuum line shunt 66 remains held open for a short time so that the vacuum circuit is open to the atmosphere through a third biological exit filter 63. This prevents a vacuum level to be built up instantaneously. Within a second or two after startup, control circuit 69 closes valve 67. With the breast cups attached to the pump by way of the first biological isolation filter 23, the vacuum circuit for the system is closed. Pump 51 then draws a vacuum in the system. The vacuum sensor 65 attached to the vacuum line 64 continuously monitors the level of vacuum in the system. The vacuum sensed at this location is a good indicator of the vacuum being applied to the breast cups. When the vacuum level reaches a threshold level set by the front panel control 19, the control circuit 69 causes the valve 67 to open for a short period of time to cause the vacuum level in line 64 and the system to drop. At that point, control circuit 69 will cause valve 67 to again close, allowing the vacuum to increase again. This cycle repeats until the unit is turned off completely. During the time that valve 67 is closed and the vacuum level is at the threshold set by the front panel control, pressure is being applied to the breast contained within the flexible breast cup. During the time that valve 67 is open, no pressure is applied to the breast.

Control circuit 69 contains a timer which may be a well-known type and will not be described herein. The timer is started the first time the vacuum in the system reaches the threshold level set by the front control. The start of the timer is indicated on the front panel display 17. The recommended amount of time at one sitting should not exceed 20 minutes. The display on the front panel is there to assist the user in not exceeding the recommended amount of time for one sitting. The timer in control circuit 69 is reset only when the unit is powered off.

Two vacuum threshold levels are controlled by control circuit 69. The first threshold level is set by the user using front panel control 19. The second, a higher vacuum level, used as a safety threshold, is stored within control circuit 69. When the second level is sensed by vacuum sensor 65, control circuit 69 shuts down the pump. This would occur only if the valve 67 malfunctions, or for some reason valve 67 is unable to release the vacuum in the system.

The pump of the present invention takes into account the physiological refractory time that is inherent in the normal function of a breast during a milking cycle. By physiological refractory time is meant that part of a feeding or pumping cycle that starts after the milk has been ejected from the breast and ends with the refilling of the breast chambers with milk prior to the next pressure-induced ejection of milk.

The breast pump of the present invention gives the user the ability to adjust the pump to allow for refilling of the breast chambers between pressure cycles. The result is the amount of milk collected in any given time is substantially increased and the physical demands on the mother are concomitantly reduced.

The present breast pump implements an electronic refractory time to track the physiological refractory time of the individual user. The electronic refractory time of the present invention is defined as the beginning of an electronic pulse applied by the control circuit 69 to valve 67 causing the valve to close and create a vacuum in the breast cup. The frequency of the pulse is independent of the pulse width that controls the time the valve 67 is closed. A negative pressure to the breast cups for a certain duration as determined by the pulse width that is applied keeps the valve closed. The user selects the dwell time, the time during which a cup is applying pressure to the breast by adjusting control knob 21.

Adjusting control knob 21 which controls the dwell time also effectively adjusts the amount of time between pulses, a time of little or no pressure. This time is needed for replenishment of the milk supply to the breast. The dwell time adjustment does not affect the frequency of the pulses being supplied to valve 67. It only adjusts the dwell time, the amount of time pressure is applied. Thus, shortening or lengthening the dwell time, i.e., the pulse durations, also lengthens or shortens the time between the pulses. In this manner, the time needed for replenishment of the milk supply to the breast, the physiological refractory time is adjusted. It has been found that the ability of the user to adjust the electronic refractory time, to suit the individual physiological differences of the user adds considerably to the comfort level of the user. The pump cycle can be adjusted by the user in the preferable range of 28-60 cycles/minute.

The breast pump system of the present invention is constructed to utilize a plurality of separate and individualized milk capture systems, each one isolated by their respective separate filters, in order to protect the individual user and prevent contamination between the equipment and the user. The filters utilized are inserted into the vacuum line between the collection bottles and the pump. The first and perhaps most important filter is the first biological input filter 23 which functions to isolate the milk and the user from the pump. The importance of this biological isolation has been studied and chronicled in a variety of scholarly articles such as the article entitled "Contaminated Breast Milk: A Source of *Klebsiella Bacteremia* in a Newborn Intensive Care Unit," Volume 3, No. 4, of *Reviews of Infectious Diseases*, July/August 1981; "Infection Risks From Electrically Operated Breast Pumps" in *Journal of Hospital Infection* 1989; and "Evaluation of Vacuum Suction Safety Devices in Preventing Transmission of Human Virus Pathogens" in *American Clinical Laboratory*, January 1989.

The first biological isolation filter 23 is made to be easily connected and disconnected and disposable. It is envisioned that each individual user would have her own set of breast cups and biological filter which is simply push-connected to the housing unit 13.

A second filter 53 is located internally to the unit between the solenoid valve 67 and the input of the vacuum pump 51. The purpose of this filter is to isolate the vacuum pump from the solenoid valve in case of valve failure.

A third exit filter 63 is located in series with the outlet or positive pressure side of the vacuum pump 51. This particular filter prevents dispersal of aerosols and contaminants in the atmosphere surrounding the pump and thereby reduces the possibility of cross-contamination.

The breast pump of the present invention is unique in this industry in that the pressure that is applied to the milk collection system, i.e., the breast cups, is continuously monitored, utilizing an electronic system composed of a solid state pressure transducer and its associated circuitry. The information provided by the transducer causes the logic circuits to control an electronic valve in the vacuum system. Furthermore, the breast pump is designed to provide fail-safe operation by continuously monitoring the pressure applied to the breast cups.

Figure 9:
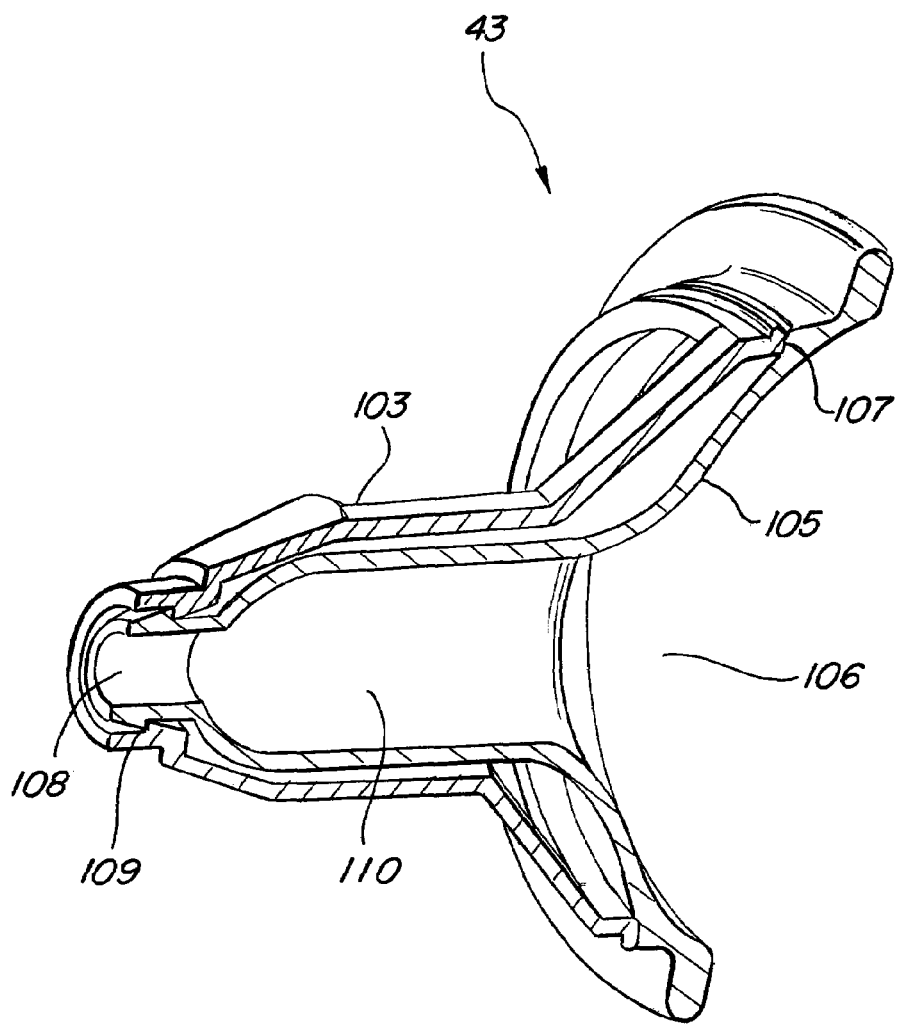
FIG. 9 is a cut-away sectional perspective illustration of a preferred embodiment of the breast pump.
Figure 11:
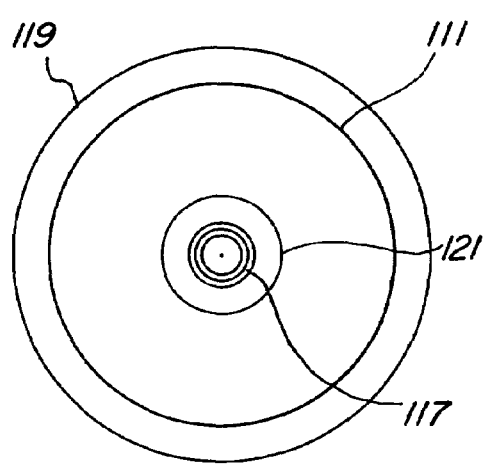
FIG. 11 is a front plan view of the breast cup to form the small first end.

A preferred embodiment of a breast cup 43 is illustrated in FIG. 9 as a two-part assembly of a molded holder 103 and a breast cup 105 which is held within the molded holder 103 at a larger second end 107 of holder 103 and at a smaller first end 109 of holder 103. The large second end 107 is connected to the smaller first end by ribs 104. The holder 103 is preferably made from an ABS plastic material molded to the preferred shape shown. The breast cup 105 is preferably molded from a biocompatible silicone material which is flexible. The large second end opening 106 of the breast cup or FIG. 9 is sized to accept a portion of a human breast for many different sized women with the teat of the breast extending into the narrow middle area 110 of the breast cup 105. The small opening 108 in the first end of the breast cup 43 is designed for fastening to a vacuum line. When a vacuum is pulled at opening 108, the breast cup 105 will collapse in a controlled sequential manner that mimics a suckling infant, as will be explained hereinafter.

Figure 10:
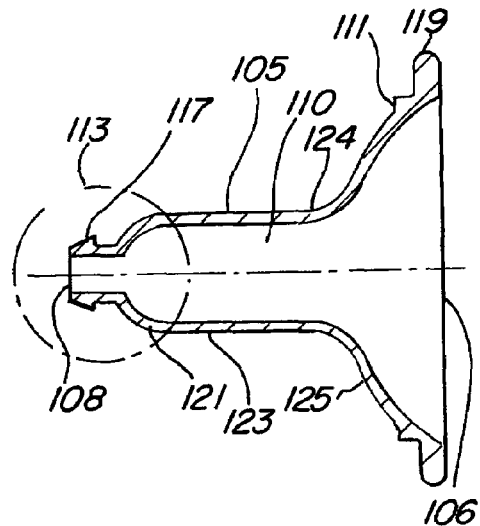
FIG. 10 is a cross-section taken along the length of the breast cup preferred embodiment.
Figure 12:
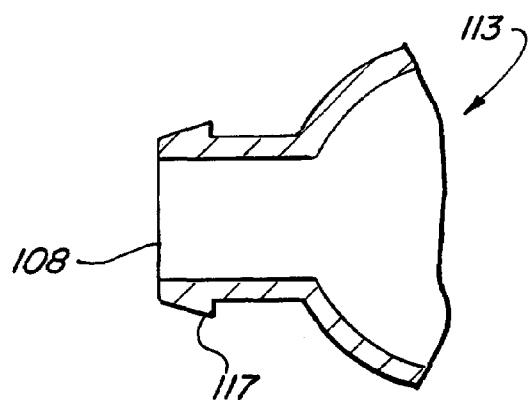
FIG. 12 is an expanded view for purposes of illustrating the small first end of the breast cup of FIG. 10.

Referring now to FIG. 10 which shows a cross-section of the breast cup 105 along its length, the structure of the breast cup is more readily illustrated. The first end opening 108 has a cross-sectional diameter of approximately half-inch or less, as shown by the exploded Section 113 in FIG. 12. A wedge-type ridge 117 is formed at the extreme end. This ridge interacts with a complementary ridge 109 on the inside of the holder 103 as shown in FIG. 9. The first end is preferably about 0.175 inches thick, providing fairly rigid support for the fastening wedge 117. At the first radius 121, the cross-sectional diameter of the breast cup increases to about one inch. The wall thickness at this point remains about the same. The wall thickness remains constant to the next radius 124. The length of the cup from the small first end opening 108 to radius 124 is about two-thirds the length of the entire cup 105. At the radius 124, the cup size expands in a cone-shape manner to the second and large open end 106 which is approximately 3.5 inches in diameter. Open end 106 has a thickened ridge 119 defining its outer perimeter which adds stability to the second end of the breast cup. Adjacent to the ridge 119 is a platform 111 which forms a stable base for the second end 107 of the holder 103 (FIG. 9) to rest on.

The thickness of the wall of the cup at point 125, just beyond the radius 124, where the cup enlarges in a cone-shaped manner is chosen to be less than the thickness of the walls at 123 and at the second end 119. As a result of this cross-sectional wall thickness variation, when a vacuum is applied to the opening 108 at the first end of the cup, the cup will collapse first at area 125 on the cup which is located on the areola area of the human breast when the human breast is located in the cup. The collapse of cup 105 in this manner causes the areola of the human breast to be squeezed first, and then the teat which is located in the center 110 of the elongated section between radius 121 and 124 of the breast cup. This controlled collapse replicates the mechanical forces of a suckling infant and causes the expression of milk in a more efficient and comfortable manner.

Figure 13:
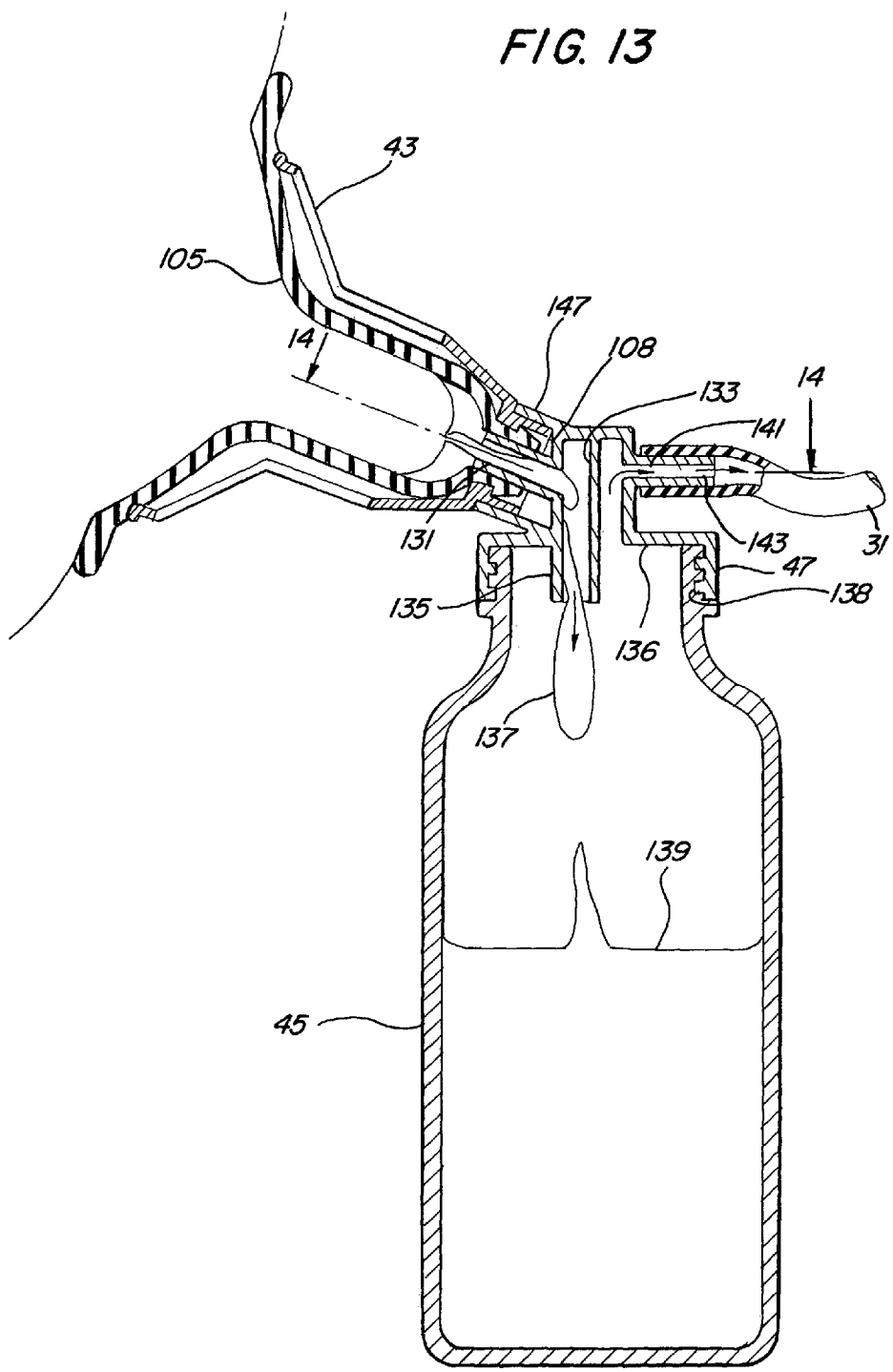
FIG. 13 is a cross-sectional view of a cup connected to a bottle cap pursuant to a preferred embodiment of this invention.
Figure 14:
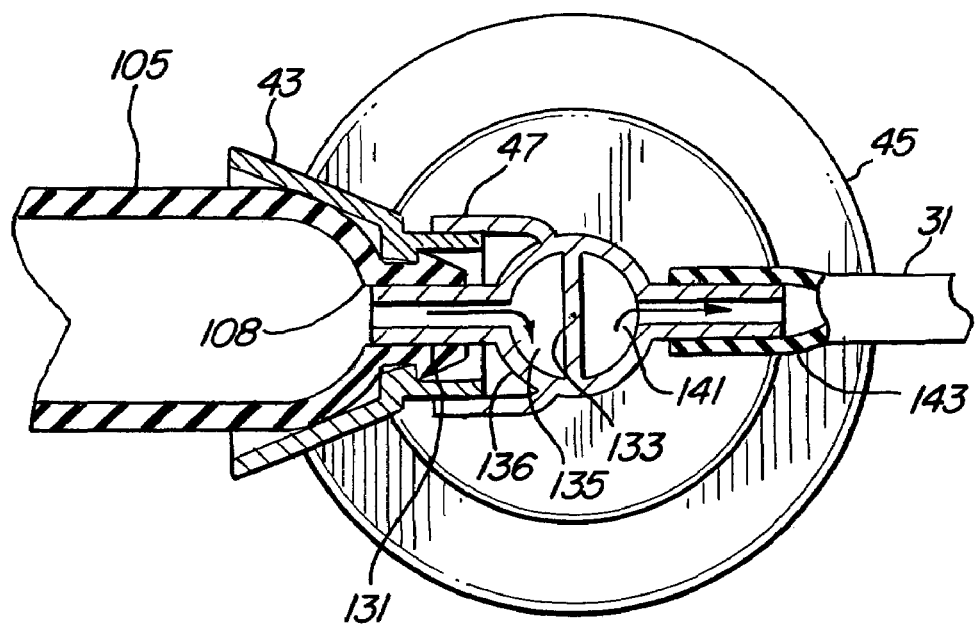
FIG. 14 is a cross-section along lines 14-14 of FIG. 13 showing the preferred construction of the bottle cap.

Referring now to FIGS. 13 and 14 which illustrate in greater detail the bottle cap 47 for the milk collection bottle 45, the breast cup 43 is shown connected to female receptacle 147 on cap 47. Vacuum tube 31 is shown connected to male tube connector 143. The narrow discharge end of the flexible cup 105 has an opening 108 therein which receives the hollow male extension 131 located in receptacle 147, when the narrow end of the breast cup assembly 43 is inserted into receptacle 147. The result is a vacuum-type connection between the breast cup 105 and the collection bottle 45.

The other end of the hollow male extension 133 connects to a hollow tube 135 which, in its preferred embodiment, is semi-circular in shape with one wall 133 being flat and the other wall 136 being rounded. Tube 135 extends down below the surface of the closed end 136 of cap 47 which has internal threads 138 located therein to engage external threads on the bottom 45.

The length of tube 135 below the closed end 136 is chosen so that the separation between the discharge end of tube 135 which discharges the mother's milk 137 into the bottle 45 is a sufficient distance away from the opening of tube connector 143 so that there is no splash back into tube connector 143 of the mother's milk 137 dropping into bottle 45, or any milk 139 contained in the bottle splashing up into the opening of tube connector 143.

In operation, the breast pump creates a vacuum in vacuum line 31 causing evacuation of all air 141 contained in bottle 45 and air contained in breast cup 105 between its discharge opening 108 and the other end when it is closed by a human breast. The vacuum in both the bottle 45 and in the breast cup 105 causes external forces to collapse cup 105 according to the vacuum cycle selected. As explained hereinabove, this cycle creates the mechanical forces of a suckling infant that causes the expression of the mother's milk 137 into the collecting bottle 45. The design of the cap 47 as shown in FIGS. 13 and 14 specifically prevents any contamination of the vacuum system by the mother's milk 137 being expressed into the bottle, or the milk 139 contained in the bottle, being pulled into the vacuum tube connector 143.

What is claimed is:

1. A breast cup assembly comprising:
   a bottle attachment end for connecting to a vacuum source;
   a large open end opposite the bottle attachment end for accepting a woman's breast;
   a holder comprising:
       a small end residing proximal to the bottle attachment end of the breast cup assembly and including a holder engaging feature;
       a large end opposite the small end and having a larger diameter than the small end; and
       a center portion connecting the small end to the large end, the center portion having at least one cut out passing radially through the holder to allow free movement inside the holder;
   a single layer breast cup made of biocompatible material and supported inside the holder, the breast cup having an inner surface exposed to the vacuum source and an outer surface exposed to atmospheric pressure, the breast cup sequentially comprising;
       a connecting portion residing proximal to the bottle attachment end of the breast cup assembly and including a cup engaging feature engaged by the holder engaging feature of the small end of the holder for retaining the breast cup in the holder; the connecting portion connectable to the vacuum source;
       a cylindrical middle area formed contiguous to the connecting portion, and configured for receiving a teat of a breast and having a first thickness; and
       a cone shaped portion formed contiguous to the middle area, and configured for receiving a portion of the breast, the cone shaped portion increasing in diameter away from the middle area to the large open end, and supported proximal to the large open end by the large end of the holder, the cone shaped portion having a second thickness,
   wherein the second thickness is less than the first thickness so that upon application of vacuum to the connecting portion the cone shaped portion distorts before the mid portion distorts.

2. The breast cup assembly of claim 1, wherein:
the center portion of the holder comprises at least two ribs connecting the small end to the large end; and
gaps between the ribs provide the cut out to allow free movement of the breast cup inside the holder.

3. The breast cup assembly of claim 2, wherein the cone shaped portion of the breast cup includes a thickened ridge for adding stability to the large open end of the breast cup assembly and a platform proving a stable base for the large end of the holder.

4. The breast cup assembly of claim 3, wherein the entire inner surfaces of the middle area of the breast cup and the cone shaped portion of the breast cup are exposed to the vacuum source and the entire outer surfaces of the middle area of the breast cup and the cone shaped portion of the breast cup, with the exception the platform of the cone shaped portion, are exposed to the atmospheric pressure.

5. The breast cup assembly of claim 2, further including a smooth radius transitioning from the cylindrical middle area to the cone shaped portion.

6. The breast cup assembly of claim 1, wherein;
the cup engaging feature comprises a fastening wedge and the holder engaging feature comprises a complementary ridge; and
the connecting portion of the breast cup is insertable into the small end of the holder so that the fastening wedge catches on the complementary ridge to retain the breast cup in the holder.

7. The breast cup assembly of claim 6, wherein;
the fastening wedge is frusto conical in shape decreasing in diameter toward the front of the breast cup and having a rearward facing wedge face extending inward; and
the complementary ridge includes a forward facing ridge face for cooperation with the wedge face to retain the breast cup in the holder.

8. The breast cup assembly of claim 1, wherein the cylindrical middle area is about one inch in diameter.

9. The breast cup assembly of claim 8, wherein the large open end is about 3.5 inches in diameter.

10. The breast cup assembly of claim 1, wherein the connecting portion and the middle area of the breast cup comprise approximately ⅔ of the total length of the breast cup and the cone shaped portion comprises approximately ⅓ of the total length of the breast cup.

11. The breast cup assembly of claim 1, wherein the first thickness of the breast cup is about 0.175 inches.

12. The breast cup assembly of claim 1, wherein the breast cup is made from silicone rubber.

13. A breast cup assembly comprising:
a bottle attachment end for connecting to a vacuum source;
a large open end opposite the bottle attachment end for accepting a woman's breast;
a holder comprising:
a round cross-section small end residing proximal to the bottle attachment end of the breast cup assembly and including an internal passage with a forward facing ridge face;
a round cross-section large end opposite the small end and having a larger diameter than the small end; and
a center portion connecting the small end to the large end, the center portion having at least one cut out passing radially through the holder to allow free movement inside the holder;
a single layer breast cup made of biocompatible material and supported inside the holder, the breast cup having an inner surface exposed to the vacuum source and an outer surface exposed to atmospheric pressure, the breast cup sequentially comprising;
a connecting portion residing proximal to the bottle attachment end of the breast cup assembly and supported by the small end of the holder and including a fastening wedge tapering small to the front of the breast cup and including a rearward facing wedge face; the connecting portion for connecting to the vacuum source;
a cylindrical middle area formed adjacent to the connecting portion, and configured for receiving a teat of a breast; and
a cone shaped portion formed adjacent to the middle area, and configured for receiving a portion of the breast, the cone shaped portion increasing in diameter away from the mid portion to the large open end, and supported proximal to the large open end by the large end of the holder,
wherein the breast cup assembly is formed by inserting the breast cup into the holder wherein the fastening wedge catches on the complementary ridge to retain the breast cup in the holder.

14. The breast cup assembly of claim 13, wherein;
the fastening wedge is frusto conical in shape decreasing in diameter toward the front of the breast cup and having a rearward facing wedge face extending inward; and
the complementary ridge includes a forward facing ridge face for cooperation with the wedge face.

15. The breast cup assembly of claim 14, wherein:
the center portion of the holder comprises at least two ribs connecting the small end to the large end; and
gaps between the ribs provide the cut out to allow free movement of the breast cup inside the holder.

16. The breast cup assembly of claim 13, wherein the cone shaped portion of the breast cup includes a thickened ridge for adding stability to the large open end of the breast cup assembly and a platform providing a stable base for the large end of the holder.

17. The breast cup assembly of claim 13, wherein;
the cylindrical middle area has a first thickness;
the cone shaped portion has a second thickness; and
the second thickness is less than the first thickness so that upon application of vacuum to the connecting portion the cone shaped portion distorts before the mid portion distorts.

18. A breast cup assembly comprising:
a bottle attachment end for connecting to a vacuum source;
a large open end opposite the bottle attachment end for accepting a woman's breast;
a holder comprising:
a round cross-section small end residing proximal to the bottle attachment end of the breast cup assembly;
a round cross-section large end opposite the small end and having a larger diameter than the small end; and
a center portion connecting the small end to the large end, the center portion having at least one cut out passing radially through the holder to allow free movement inside the holder;
a single layer breast cup made of biocompatible material and supported inside the holder, the breast cup having an inner surface exposed to the vacuum source and an outer surface exposed to atmospheric pressure, the breast cup sequentially comprising;

a connecting portion residing proximal to the bottle attachment end of the breast cup assembly and insertable into the small end of the holder, wherein the connection portion includes an interior surface for receiving a vacuum source and an exterior surface for cooperation with the small end of the holder wherein insertion of the vacuum source into the connecting portion biases the exterior surface of the connecting portion against the small end of the holder to hold the breast cup in the holder;

a cylindrical middle area formed adjacent to the connecting portion, and configured for receiving a teat of a breast; and a cone shaped portion formed adjacent to the middle area, and configured for receiving a portion of the breast, the cone shaped portion increasing in diameter away from the mid portion to the large open end, and supported proximal to the large open end by the large end of the holder, wherein the breast cup assembly is formed by inserting the breast cup into the holder wherein a fastening wedge on the connecting portion of the breast cup catches on a complementary ridge of the small end of the holder to retain the breast cup in the holder.

19. The breast cup assembly of claim 18, wherein;
the cylindrical middle area has a first thickness;
the cone shaped portion has a second thickness; and
the second thickness is less than the first thickness so that upon application of vacuum to the connecting portion the cone shaped portion distorts before the mid portion distorts.

20. The breast cup assembly of claim 18, wherein:
the cone shaped portion of the breast cup includes a thickened ridge for adding stability to the large open end of the breast cup assembly and a platform proving a stable base for the large end of the holder; and
the entire inner surfaces of the middle area of the breast cup and the cone shaped portion of the breast cup are exposed to the vacuum source and the entire outer surfaces of the middle area of the breast cup and the cone shaped portion of the breast cup, with the exception the platform of the cone shaped portion, are exposed to the atmospheric pressure.

21. A breast cup assembly comprising:
a bottle car having a hollow male extension and a vacuum attachment section;
a holder comprising:
    a small end residing proximal to the bottle cap of the breast cup assembly;
    a large end opposite the small end and having a larger diameter than the small end; and
    a center portion connecting the small end to the large end, the center portion having at least one cut out passing radially through the holder to allow free movement inside the holder;
a single layer breast cup made of biocompatible material and supported inside the holder, the breast cup having an inner surface exposed to a vacuum source and an outer surface exposed to atmospheric pressure, the breast cup sequentially comprising;
    a connecting portion residing proximal to the bottle attachment end of the breast cup assembly and supported by the small end of the holder; the connecting portion receiving the hollow male extension connecting the breast cup to the vacuum source;
    a cylindrical middle area formed contiguous to the connecting portion and configured for receiving a teat of a breast and having a first thickness; and
    a cone shaped portion formed contiguous to the middle area, and configured for receiving a portion of the breast, the cone shaped portion increasing in diameter away from the middle area to the large open end, and supported proximal to the large end of the holder, the cone shaped portion having a second thickness,
    wherein the second thickness is less than the first thickness so that upon application of vacuum to the connecting portion the cone shaped portion collapses and then the cylindrical middle area collapses thereby mimicking the suckling of an infant.

* * * * *